United States Patent
Peng et al.

(10) Patent No.: US 12,183,003 B2
(45) Date of Patent: Dec. 31, 2024

(54) PET QUANTITATIVE LOCALIZATION SYSTEM AND OPERATION METHOD THEREOF

(71) Applicants: Taipei Medical University (TMU), Taipei (TW); TAIPEI VETERANS GENERAL HOSPITAL, Taipei (TW)

(72) Inventors: Syu-Jyun Peng, Hsinchu County (TW); Hsiang-Yu Yu, Taipei (TW); Yen-Cheng Shih, Taipei (TW); Tse-Hao Lee, Taipei (TW)

(73) Assignees: Taipei Medical University (TMU), Taipei (TW); TAIPEI VETERANS GENERAL HOSPITAL, Taipei (TW)

( * ) Notice: Subject to any disclaimer, the term of this patent is extended or adjusted under 35 U.S.C. 154(b) by 375 days.

(21) Appl. No.: 17/452,238

(22) Filed: Oct. 26, 2021

(65) Prior Publication Data
US 2022/0398732 A1 Dec. 15, 2022

(30) Foreign Application Priority Data
Jun. 15, 2021 (TW) ................................. 110121785

(51) Int. Cl.
*G06T 7/00* (2017.01)
*A61B 6/00* (2024.01)
(Continued)

(52) U.S. Cl.
CPC ............ *G06T 7/0014* (2013.01); *A61B 6/037* (2013.01); *A61B 6/501* (2013.01); *A61B 6/5247* (2013.01);
(Continued)

(58) Field of Classification Search
CPC ........... G06T 7/0014; G06T 5/50; G06T 5/70; G06T 7/11; G06T 7/136; G06T 7/30;
(Continued)

(56) References Cited

U.S. PATENT DOCUMENTS 10,945,685 B2 * 3/2021 Li ............................. G06T 5/50
2020/0029918 A1 * 1/2020 Li .......................... G06T 7/0012
(Continued)

FOREIGN PATENT DOCUMENTS

CN  103181762 B  5/2015
CN  109965895 A  7/2019
(Continued)

OTHER PUBLICATIONS

Yi-Min Huang, The Study of Kidney Function in MRI Scans, Institute of Multimedia Engineering National Chiao Tung University, Master Thesis, Oct. 2007.

*Primary Examiner* — Nancy Bitar
*Assistant Examiner* — Heath E. Wells
(74) *Attorney, Agent, or Firm* — CKC & Partners Co., LLC

(57) ABSTRACT

The present disclosure provides an operation method of a PET (positron emission tomography) quantitative localization system, which includes steps as follows. The PET image and the MRI (magnetic resonance imaging) of the patient are acquired; the nonlinear deformation is performed on the MRI and the T1 template to generate deformation information parameters; the AAL (automated anatomical labeling) atlas is deformed to an individual brain space of the patient, so as to generate an individual brain space AAL atlas, where the AAL atlas and the T1 template are in a same space; lateralization indexes of the ROIs of the individual brain space AAL atlas corresponding to the PET image normalized through the gray-scale intensity are calculated; the lateralization indexes are inputted into one or more machine learning models to analyze the result of determining a target.

12 Claims, 2 Drawing Sheets

(51) Int. Cl.
  *A61B 6/03*   (2006.01)
  *A61B 6/50*   (2024.01)
  *G06T 5/50*   (2006.01)
  *G06T 5/70*   (2024.01)
  *G06T 7/11*   (2017.01)
  *G06T 7/136*  (2017.01)
  *G06T 7/30*   (2017.01)

(52) U.S. Cl.
  CPC ............... *G06T 5/50* (2013.01); *G06T 5/70* (2024.01); *G06T 7/11* (2017.01); *G06T 7/136* (2017.01); *G06T 7/30* (2017.01); *G06T 2207/10088* (2013.01); *G06T 2207/10104* (2013.01); *G06T 2207/20081* (2013.01); *G06T 2207/30016* (2013.01)

(58) Field of Classification Search
  CPC . G06T 2207/10088; G06T 2207/10104; G06T 2207/20081; G06T 2207/30016; G06T 2207/20128; A61B 6/037; A61B 6/501; A61B 6/5247; A61B 5/0035; A61B 5/0042; A61B 5/055; A61B 5/4064; A61B 6/4417; A61B 6/5205; A61B 6/5217; G06V 2201/03
  USPC ......................................................... 382/131
  See application file for complete search history.

(56) References Cited

U.S. PATENT DOCUMENTS

2021/0150671 A1* 5/2021 Guo ..................... G16H 30/40
2022/0051402 A1* 2/2022 Dikici ................... G06T 7/0012

FOREIGN PATENT DOCUMENTS

TW              I680744 B        1/2020
WO      WO-2022132772 A1 *  6/2022
WO      WO-2022232688 A1 * 11/2022

* cited by examiner

PET QUANTITATIVE LOCALIZATION SYSTEM AND OPERATION METHOD THEREOF

RELATED APPLICATIONS

This application claims priority to Taiwan Patent Application No. 110121785, filed Jun. 15, 2021, the entirety of which is herein incorporated by reference.

BACKGROUND

Field of Invention

The present invention relates to systems and methods, and more particularly, PET (positron emission tomography) quantitative localization systems and operation methods thereof.

Description of Related Art

The medial temporal lobe epilepsy is a common epilepsy in adults, and hippocampal sclerosis is the most commonly seen pathology. Surgical resection of epileptogenic foci can achieve freedom from seizures in 60-80% patients, thereby improving the quality of life of patients and returning to normal social functions. The successful surgery is based on the accuracy of preoperative localization of epileptogenic foci. The preoperative evaluation includes MRI (magnetic resonance imaging), long-term EEG recording, neuropsychological examination and PET (positron emission tomography). For patients with mild hippocampal sclerosis, the preoperative neuroimage sometimes exhibit no significantly change or is atypical, and therefore it difficult to determine the epilepsy lesion.

For example, the commonly used radioactive tracer in PET is $^{18}$F-fluorodeoxyglucose (FDG). Metabolic decline could be observed in 85-90% of temporal lobe epilepsy, and this feature can help determine the side of the epilepsy lesion. Currently, the determination is based on the subjective comparison of the asymmetry of the PET image on both sides of the medial temporal lobes by human eyes in clinical practice. The standardized quantitative analysis has not been widespread adopted and not easy to access for clinician. When the difference between the two sides is not large, the visual analysis cannot obtain reliable results, which can cause unconcordant results with other pre-surgical evaluation. Therefore, the patient may need the second stage of invasive intracranial electrode implantation to determine the condition of epilepsy lesions.

SUMMARY

In one or more various aspects, the present disclosure is directed to PET (positron emission tomography) quantitative localization systems and operation methods thereof.

An embodiment of the present disclosure is related to a PET quantitative localization system. The PET quantitative localization includes a memory circuit and a processor. The memory circuit is configured to store at least one instruction. The processor is coupled to the memory circuit, and the processor configured to access and execute the at least one instruction for: acquiring a PET image and a MRI (magnetic resonance imaging) of at least one patient; performing a nonlinear deformation spatial registration on the MRI and a T1 template to generate a deformation information parameter; deforming an AAL (automated anatomical labeling) atlas to an individual brain space of the at least one patient through the deformation information parameter, so as to generate an individual brain space AAL atlas, where the AAL atlas and the T1 template are in a same space; calculating a plurality of lateralization indexes of a plurality of ROIs (regions of interest) of the individual brain space AAL atlas corresponding to the PET image processed through a intensity normalization; inputting the lateralization indexes into at least one machine learning model, so as to analyze a result of determining a target.

In one embodiment of the present disclosure, the processor accesses and executes the at least one instruction for: linearly co-registering the PET image to the MRI, so as to generate a co-registered PET image; smoothing the co-registered PET image to generate a smoothed PET image; performing a brain tissue segmentation on the MRI to obtain a whole brain gray matter density image; binarizing the whole brain gray matter density image by a threshold value to generate a whole brain gray matter mask; performing the intensity normalization on the smoothed PET image to obtain the PET image processed through the intensity normalization based on an average of PET standardized uptake values corresponding to the whole brain gray matter mask.

In one embodiment of the present disclosure, the ROIs includes a plurality of left brain ROIs and a plurality of right brain ROIs, and the processor accesses and executes the at least one instruction for: selecting a plurality of left-side standardized uptake values corresponding to the left brain ROIs and a plurality of right-side standardized uptake values corresponding to the right brain ROIs from the PET image processed through the intensity normalization; calculating the lateralization indexes based on a difference between the left standardized uptake values and the right standardized uptake values.

In one embodiment of the present disclosure, each of the lateralization indexes satisfies a following calculation: 2×(the left standardized uptake value−the right standardized uptake value)÷(the left standardized uptake value+the right standardized uptake value).

In one embodiment of the present disclosure, the PET image and the MRI of the at least one patient includes a plurality of PET images and a plurality of MRIs of a plurality of patients, the at least one machine learning model includes a plurality of different machine learning models, and the processor accesses and executes the at least one instruction for: inputting the lateralization indexes of each of the patients into the different machine learning models, and selecting one machine learning model having a highest accuracy of determining the target from the different machine learning models.

Another embodiment of the present disclosure is related to an operation method of a PET quantitative localization. The operation method includes steps of: acquiring a PET image and a MRI of at least one patient; performing a nonlinear deformation spatial registration on the MRI and a T1 template to generate a deformation information parameter; deforming an AAL atlas to an individual brain space of the at least one patient through the deformation information parameter, so as to generate an individual brain space AAL atlas, where the AAL atlas and the T1 template are in a same space; calculating a plurality of lateralization indexes of a plurality of ROIs of the individual brain space AAL atlas corresponding to the PET image processed through a intensity normalization; inputting the lateralization indexes into at least one machine learning model, so as to analyze a result of determining a target.

In one embodiment of the present disclosure, the operation method further includes steps of: linearly co-registering the PET image to the MRI, so as to generate a co-registered PET image; smoothing the co-registered PET image to generate a smoothed PET image; performing a brain tissue segmentation on the MRI to obtain a whole brain gray matter density image; binarizing the whole brain gray matter density image by a threshold value to generate a whole brain gray matter mask; performing the intensity normalization on the smoothed PET image to obtain the PET image processed through the intensity normalization based on an average of PET standardized uptake values corresponding to the whole brain gray matter mask.

In one embodiment of the present disclosure, the ROIs includes a plurality of left brain ROIs and a plurality of right brain ROIs, and the step of calculating the lateralization indexes of the ROIs of the individual brain space AAL atlas corresponding to the PET image processed through a intensity normalization includes: selecting a plurality of left-side standardized uptake values corresponding to the left brain ROIs and a plurality of right-side standardized uptake values corresponding to the right brain ROIs from the PET image processed through the intensity normalization; calculating the lateralization indexes based on a difference between the left standardized uptake values and the right standardized uptake values.

In one embodiment of the present disclosure, each of the lateralization indexes satisfies a following calculation: 2×(the left uptake value−the right uptake value)÷(the left uptake value+the right uptake value).

In one embodiment of the present disclosure, the PET image and the MRI of the at least one patient includes a plurality of PET images and a plurality of MRIs of a plurality of patients, the at least one machine learning model includes a plurality of different machine learning models, and the step of inputting the lateralization indexes into the at least one machine learning model includes: inputting the lateralization indexes of each of the patients into the different machine learning models, and selecting one machine learning model having a highest accuracy of determining the target from the different machine learning models.

Technical advantages are generally achieved, by embodiments of the present disclosure. With the technical solution of the present disclosure, the quantification of PET can avoid the inaccuracy of human eye interpretation, and can assist the brain segmentation with the MRI that has a relatively high resolution.

Many of the attendant features will be more readily appreciated, as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
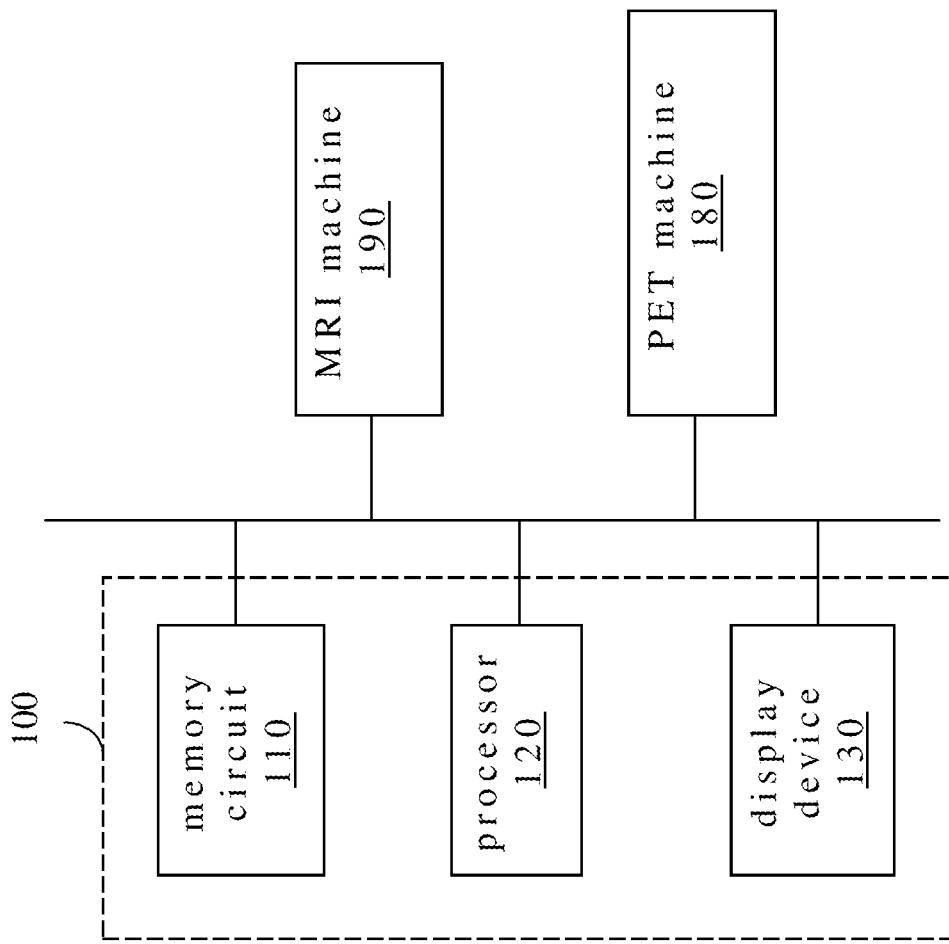
FIG. 1 is a block diagram of a PET quantitative localization system according to one embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Referring to FIG. 1, in one aspect, the present disclosure is directed to a PET quantitative localization system 100. The PET quantitative localization system 100 may be easily integrated into a computer and may be applicable or readily adaptable to all technologies. Technical advantages are generally achieved by the PET quantitative localization system 100 according to embodiments of the present disclosure. Herewith the PET quantitative localization system 100 is described below with FIG. 1.

The subject disclosure provides the PET quantitative localization system 100 in accordance with the subject technology. Various aspects of the present technology are described with reference to the drawings. In the following description, for purposes of explanation, numerous specific details are set forth in order to provide a thorough understanding of one or more aspects. It can be evident, however, that the present technology can be practiced without these specific details. In other instances, well-known structures and devices are shown in block diagram form in order to facilitate describing these aspects. The word "exemplary" is used herein to mean "serving as an example, instance, or illustration." Any embodiment described herein as "exemplary" is not necessarily to be construed as preferred or advantageous over other embodiments.

FIG. 1 is a block diagram of the PET quantitative localization system 100 according to one embodiment of the present disclosure. As shown in FIG. 1, the PET quantitative localization system 100 includes a memory circuit 110, a processor 120 and a display device 130. For example, the memory circuit 110 can be a hard drive, a flash memory or another storage device, the processor 120 can be a central processing unit, and a display device 130 can be a built-in the display screen or an external screen.

In structure, the automatic analysis system 100 is coupled to a MRI machine 190 and a PET machine 180, and the processor 120 is coupled to the memory circuit 110 and the display device 130. It should be noted that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. For example, the memory circuit 110 may be a built-in memory circuit that is directly connected to the processor 120, or the memory circuit 110 may be an external storage device that is indirectly connected to the processor 120 through the connection circuit.

In use, the memory circuit 110 store at least one instruction, the processor 120 is coupled to the memory circuit 110, and the processor 120 accesses and executes the at least one instruction for: acquiring a PET image and a MRI (magnetic resonance imaging) of at least one patient. In practice, the PET machine 180 can scan the PET image of the patient, and MRI machine 190 can get the MRI of the patient. The resolution of the MRI is higher than the resolution of the PET image. The memory circuit 110 can store the PET image and the MRI of the patient.

Then, the processor 120 accesses and executes the at least one instruction for: performing a nonlinear deformation spatial registration on the MRI and a T1 template to generate a deformation information parameter. In practice, the deformation information parameter may be a conversion matrix for subsequent applications. For example, the deformation information parameter can be DARTEL (Diffeomorphic Anatomical Registration Through Exponentiated Lie Algebra) deformation information parameter. The memory circuit 110 may pre-store the T1 template.

Then, the processor 120 accesses and executes the at least one instruction for: deforming an AAL (automated anatomical labeling) atlas to an individual brain space of the at least one patient through the deformation information parameter, so as to generate an individual brain space AAL atlas, where the AAL atlas and the T1 template are in a same space. With the individual brain space AAL atlas, data can be quantified more accurately.

Then, the processor 120 accesses and executes the at least one instruction for: calculating a plurality of lateralization indexes of a plurality of ROIs (regions of interest) of the individual brain space AAL atlas corresponding to the PET image processed through a intensity normalization; inputting the lateralization indexes into at least one machine learning model, so as to analyze a result of determining a target (e.g., the side of surgical hippocampal sclerosis). The result is generated by the at least one machine learning model. The display device 130 can display the result.

As to the PET image processed through the intensity normalization, in one embodiment of the present disclosure, the processor 120 accesses and executes the at least one instruction for: linearly co-registering the PET image to the MRI, so as to generate a co-registered PET image, thereby maintaining the consistency of spatial data coordinates; smoothing the co-registered PET image to generate a smoothed PET image, thereby improving the signal-to-noise ratio; performing a brain tissue segmentation on the MRI to obtain a whole brain gray matter density image, in which the MRI that has a relatively high resolution assists the brain tissue segmentation accurately; binarizing the whole brain gray matter density image by a threshold value (e.g., 0.5) to generate a whole brain gray matter mask; performing the intensity normalization on the smoothed PET image to obtain the PET image processed through the intensity normalization based on an average of PET standardized uptake values corresponding to the whole brain gray matter mask.

As to above ROIs, in one embodiment of the present disclosure, the ROIs includes a plurality of left brain ROIs and a plurality of right brain ROIs, and the processor 120 accesses and executes the at least one instruction for: selecting a plurality of left-side standardized uptake values corresponding to the left brain ROIs and a plurality of right-side standardized uptake values corresponding to the right brain ROIs from the PET image processed through the intensity normalization; calculating the lateralization indexes based on a difference between the left standardized uptake values and the right standardized uptake values. In practice, the left brain ROIs can be the left hippocampal gyrus and related brain regions (e.g., a left amygdala), and the right brain ROIs can be the right hippocampal gyrus and related brain regions (e.g., a right amygdala).

As to the calculation of the lateralization indexes, in one embodiment of the present disclosure, each of the lateralization indexes satisfies a following calculation: 2×(the left standardized uptake value−the right standardized uptake value)÷(the left standardized uptake value+the right standardized uptake value). In practice, taking one ROI being the hippocampal gyrus as an example, the left hippocampal gyrus and right hippocampal gyrus correspond to each other, the left standardized uptake value is an standardized uptake value of the left hippocampal gyrus in the PET image processed through the intensity normalization, and the right standardized uptake value is an standardized uptake value of the right hippocampal gyrus in the PET image processed through the intensity normalization. The other left and right side standardized uptake values of the other ROIs can be deduced in the similar manner, and thus, the present disclosure is not repeated herein.

In one embodiment of the present disclosure, the PET image and the MRI of the at least one patient includes a plurality of PET images and a plurality of MRIs of a plurality of patients, the at least one machine learning model includes a plurality of different machine learning models, and the processor 120 accesses and executes the at least one instruction for: inputting the lateralization indexes of each of the patients into the different machine learning models, and selecting one machine learning model having a highest accuracy of determining the target from the different machine learning models. Clinically, for example, the machine learning model with the highest accuracy can be used to provide auxiliary interpretation.

In a control experiment, the software provided with the PET machine 180 was also used as a reference. The software uses a set of norms within a certain age range as the standard to determine the difference between the brain regions of the patient and the norms. Although this control experiment has a minor quantitative concept, it has the problem in inaccurate brain segmentation.

Although it is sensitive to glucose metabolism, the spatial resolution of the FDG PET is not good, and it often needs to be combined with MRI to determine the range of specific brain regions. In the present disclosure, the high-quality MRI is automatically segmented and is combined with the FDG PET image. The average FDG positron response of individual patients' whole brain gray matter was used as the standard to measure the standardized uptake value (SUV) of each ROI. The MRI can be automatically segmented to obtain the cerebral cortex for reference. In practice, the preoperative MRI and FDG PET of a group of 93 patients with unilateral hippocampal sclerosis who had undergone surgery were used as the verification data, and this method was used to measure the PET standardized uptake values of both hippocampus and related brain regions, and use machine learning classification to verify the correctness of the determined brain side (i.e., the target), and compare the determined brain side with the result judged by the human eye.

Figure 2:
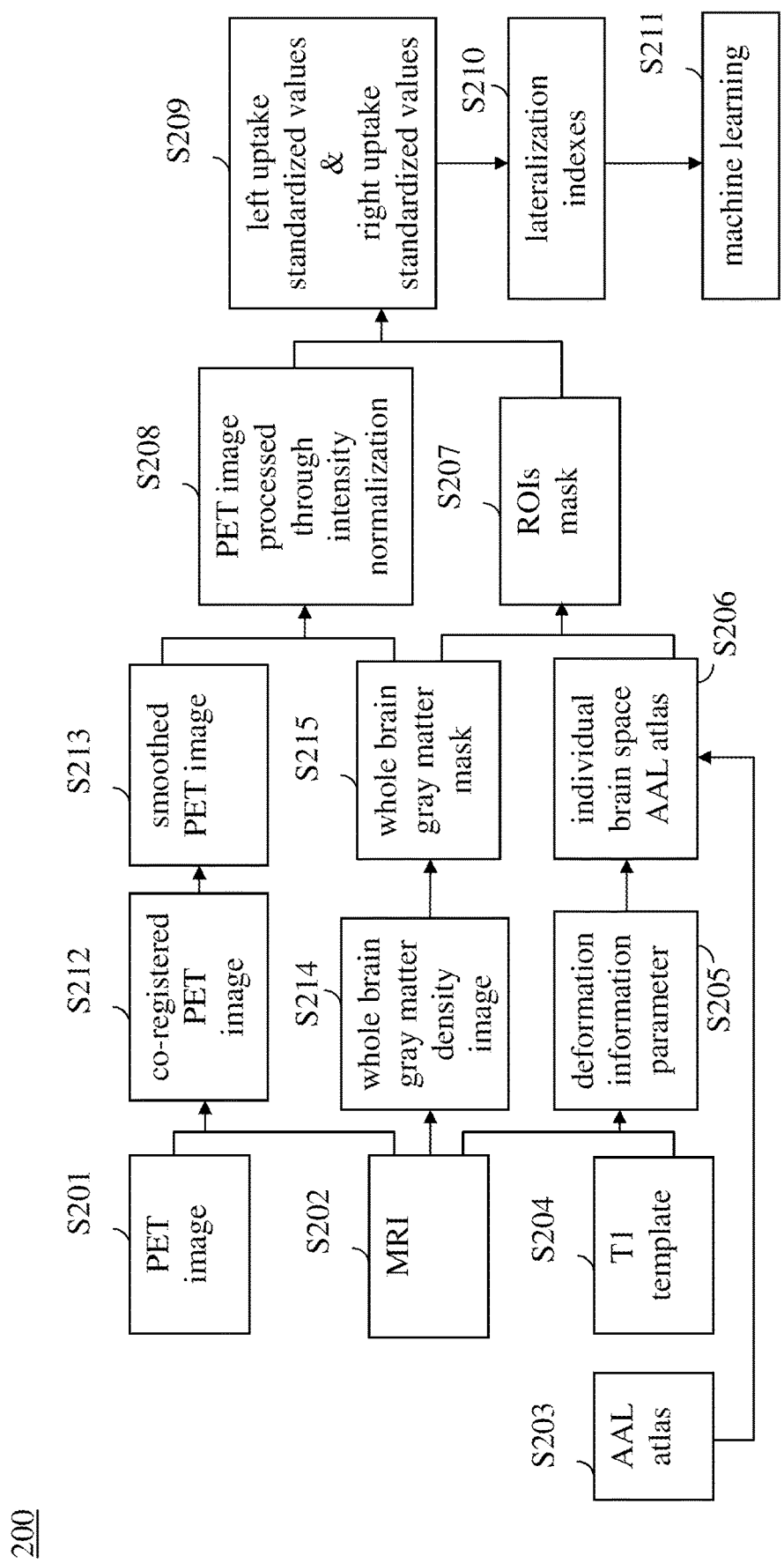
FIG. 2 is a flow chart of an operation method of the PET quantitative localization system according to one embodiment of the present disclosure.

For a more complete understanding of an operation method of the PET quantitative localization system 100, referring FIGS. 1-2, FIG. 2 is a flow chart of the operation method 200 of the PET quantitative localization system 100 according to one embodiment of the present disclosure. As shown in FIG. 2, the operation method 200 includes operations S201-S215. However, as could be appreciated by persons having ordinary skill in the art, for the steps described in the present embodiment, the sequence in which these steps is performed, unless explicitly stated otherwise, can be altered depending on actual needs; in certain cases, all or some of these steps can be performed concurrently.

The operation method 200 may take the form of a computer program product on a computer-readable storage medium having computer-readable instructions embodied in the medium. Any suitable storage medium may be used including non-volatile memory such as read only memory (ROM), programmable read only memory (PROM), erasable programmable read only memory (EPROM), and electrically erasable programmable read only memory (EEPROM) devices; volatile memory such as SRAM, DRAM, and DDR-RAM; optical storage devices such as CD-ROMs and DVD-ROMs; and magnetic storage devices such as hard disk drives and floppy disk drives.

In operation S201, a PET image of at least one patient is acquired. In operation S202, a MRI of the at least one patient is acquired. In operation S204, a T1 template is preloaded. In operation S205, the nonlinear deformation spatial registration is performed on the MRI and the T1 template to generate a deformation information parameter.

In operation S203, an AAL atlas s preloaded, where the AAL atlas and the T1 template are in the same space. In operation S206, the AAL atlas is deformed to an individual brain space of the at least one patient through the deformation information parameter, so as to generate an individual brain space AAL atlas, where the AAL atlas and the T1 template are in the same space.

In operations S207 to S210, a plurality of lateralization indexes of a plurality of ROIs of the individual brain space AAL atlas corresponding to the PET image processed through a intensity normalization are calculated. In operation S211, the lateralization indexes are inputted into at least one machine learning model, so as to analyze a result of determining a target.

In one embodiment of the present disclosure, in operation S212, the PET image is linearly co-registered to the MRI, so as to generate a co-registered PET image. In operation S213, the co-registered PET image is smoothed to generate a smoothed PET image. In operation S214, the brain tissue segmentation is performed on the MRI to obtain a whole brain gray matter density image. In operation S215, the whole brain gray matter density image is binarized by a threshold value to generate a whole brain gray matter mask; in practice, for example, the threshold value is 0.5 to obtain a better distinguishing effect. In operation S208, the intensity normalization is performed on the smoothed PET image to obtain the PET image processed through the intensity normalization based on an average of PET standardized uptake values corresponding to the whole brain gray matter mask.

In one embodiment of the present disclosure, the ROIs includes a plurality of left brain ROIs and a plurality of right brain ROIs, and the left brain ROIs correspond with the right brain ROIs. In operation S209, a plurality of left-side standardized uptake values corresponding to the left brain ROIs and a plurality of right-side standardized uptake values corresponding to the right brain ROIs are selected from the PET image processed through the intensity normalization. In operation S210, the lateralization indexes are calculated based on a difference between the left standardized uptake values and the right standardized uptake values.

In operation S210, each of the lateralization indexes satisfies a following calculation: 2×(the left standardized uptake value−the right standardized uptake value)÷(the left standardized uptake value+the right standardized uptake value).

In one embodiment of the present disclosure, the PET image and the MRI of the above-mentioned at least one patient includes a plurality of PET images and a plurality of MRIs of a plurality of patients, the above-mentioned at least one machine learning model includes a plurality of different machine learning models. In operation S211, the lateralization indexes of each of the patients are inputted into the different machine learning models, and selecting one machine learning model having a highest accuracy of determining the target from the different machine learning models.

In view of the above, technical advantages are generally achieved, by embodiments of the present disclosure. With the PET quantitative localization system 100 and its operation method 200 of the present disclosure, the quantification of PET can avoid the inaccuracy of human eye interpretation, and can assist the brain segmentation with the MRI that has a relatively high resolution.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An PET (positron emission tomography) quantitative localization system, comprising:
   a memory circuit configured to store at least one instruction; and
   a processor coupled to the memory circuit, and the processor configured to access and execute the at least one instruction for:
   acquiring a PET image and a MRI (magnetic resonance imaging) of at least one patient;
   performing a nonlinear deformation on the MRI and a T1 template to generate a deformation information parameter;
   deforming an AAL (automated anatomical labeling) atlas to an individual brain space of the at least one patient through the deformation information parameter, so as to generate an individual brain space AAL atlas, wherein the AAL atlas and the T1 template are in a same space;
   calculating a plurality of lateralization indexes of a plurality of ROIs (regions of interest) of the individual brain space AAL atlas corresponding to the PET image processed through an intensity normalization;

inputting the lateralization indexes into at least one machine learning model, so as to analyze a result of determining a target;
linearly co-registering the PET image to the MRI, so as to generate a co-registered PET image;
smoothing the co-registered PET image to generate a smoothed PET image;
performing a brain tissue segmentation on the MRI to obtain a whole brain gray matter density image;
binarizing the whole brain gray matter density image by a threshold value to generate a whole brain gray matter mask, wherein the threshold value is 0.5; and
performing the intensity normalization on the smoothed PET image to obtain the PET image processed through the intensity normalization based on an average of PET standardized uptake values corresponding to the whole brain gray matter mask.

2. The PET quantitative localization system of claim 1, wherein the ROIs comprises a plurality of left brain ROIs and a plurality of right brain ROIs, and the processor accesses and executes the at least one instruction for:
selecting a plurality of left-side standardized uptake values corresponding to the left brain ROIs and a plurality of right-side standardized uptake values corresponding to the right brain ROIs from the PET image processed through the intensity normalization; and
calculating the lateralization indexes based on a difference between the left standardized uptake values and the right standardized uptake values.

3. The PET quantitative localization system of claim 2, wherein each of the lateralization indexes satisfies a following calculation:

2×(the left standardized uptake value−the right standardized uptake value)÷(the left standardized uptake value+the right standardized uptake value).

4. The PET quantitative localization system of claim 1, wherein the PET image and the MRI of the at least one patient comprises a plurality of PET images and a plurality of MRIs of a plurality of patients, the at least one machine learning model comprises a plurality of different machine learning models, and the processor accesses and executes the at least one instruction for:
inputting the lateralization indexes of each of the patients into the different machine learning models, and selecting one machine learning model having a highest accuracy of determining the target from the different machine learning models.

5. An operation method of a PET quantitative localization system, and the operation method comprising steps of:
acquiring a PET image and a MRI of at least one patient;
performing a nonlinear deformation on the MRI and a T1 template to generate a deformation information parameter;
deforming an AAL atlas to an individual brain space of the at least one patient through the deformation information parameter, so as to generate an individual brain space AAL atlas, wherein the AAL atlas and the T1 template are in a same space;
calculating a plurality of lateralization indexes of a plurality of ROIs of the individual brain space AAL atlas corresponding to the PET image processed through an intensity normalization;
inputting the lateralization indexes into at least one machine learning model, so as to analyze a result of determining a target;
linearly co-registering the PET image to the MRI, so as to generate a co-registered PET image;
smoothing the co-registered PET image to generate a smoothed PET image;
performing a brain tissue segmentation on the MRI to obtain a whole brain gray matter density image;
binarizing the whole brain gray matter density image by a threshold value to generate a whole brain gray matter mask, wherein the threshold value is 0.5; and
performing the intensity normalization on the smoothed PET image to obtain the PET image processed through the intensity normalization based on an average of PET standardized uptake values corresponding to the whole brain gray matter mask.

6. The operation method of claim 5, wherein the ROIs comprises a plurality of left brain ROIs and a plurality of right brain ROIs, and the step of calculating the lateralization indexes of the ROIs of the individual brain space AAL atlas corresponding to the PET image processed through the intensity normalization comprises:
selecting a plurality of left-side standardized uptake values corresponding to the left brain ROIs and a plurality of right-side standardized uptake values corresponding to the right brain ROIs from the PET image processed through the intensity normalization; and
calculating the lateralization indexes based on a difference between the left standardized uptake values and the right standardized uptake values.

7. The operation method of claim 6, each of the lateralization indexes satisfies a following calculation:

2×(the left standardized uptake value−the right standardized uptake value)÷(the left standardized uptake value+the right standardized uptake value).

8. The operation method of claim 5, wherein the PET image and the MRI of the at least one patient comprises a plurality of PET images and a plurality of MRIs of a plurality of patients, the at least one machine learning model comprises a plurality of different machine learning models, and the step of inputting the lateralization indexes into the at least one machine learning model comprises:
inputting the lateralization indexes of each of the patients into the different machine learning models, and selecting one machine learning model having a highest accuracy of determining the target from the different machine learning models.

9. A non-transitory computer readable medium to store a plurality of instructions for commanding a computer to execute an operation method, and the operation method comprising steps of:
acquiring a PET image and a MRI of at least one patient;
performing a nonlinear deformation on the MRI and a T1 template to generate a deformation information parameter;
deforming an AAL atlas to an individual brain space of the at least one patient through the deformation information parameter, so as to generate an individual brain space AAL atlas, wherein the AAL atlas and the T1 template are in a same space;
calculating a plurality of lateralization indexes of a plurality of ROIs of the individual brain space AAL atlas corresponding to the PET image processed through an intensity normalization;
inputting the lateralization indexes into at least one machine learning model, so as to analyze a result of determining a target;

linearly co-registering the PET image to the MRI, so as to generate a co-registered PET image;

smoothing the co-registered PET image to generate a smoothed PET image;

performing a brain tissue segmentation on the MRI to obtain a whole brain gray matter density image;

binarizing the whole brain gray matter density image by a threshold value to generate a whole brain gray matter mask, wherein the threshold value is 0.5; and performing the intensity normalization on the smoothed PET image to obtain the PET image processed through the intensity normalization based on an average of PET standardized uptake values corresponding to the whole brain gray matter mask.

10. The non-transitory computer readable medium of claim 9, wherein the ROIs comprises a plurality of left brain ROIs and a plurality of right brain ROIs, and the step of calculating the lateralization indexes of the ROIs of the individual brain space AAL atlas corresponding to the PET image processed through the intensity normalization comprises:

selecting a plurality of left-side standardized uptake values corresponding to the left brain ROIs and a plurality of right-side standardized uptake values corresponding to the right brain ROIs from the PET image processed through the intensity normalization; and calculating the lateralization indexes based on a difference between the left standardized uptake values and the right standardized uptake values.

11. The non-transitory computer readable medium of claim 10, each of the lateralization indexes satisfies a following calculation:

$$2\times(\text{the left standardized uptake value}-\text{the right standardized uptake value})\div(\text{the left standardized uptake value}+\text{the right standardized uptake value}).$$

12. The non-transitory computer readable medium of claim 9, wherein the PET image and the MRI of the at least one patient comprises a plurality of PET images and a plurality of MRIs of a plurality of patients, the at least one machine learning model comprises a plurality of different machine learning models, and the step of inputting the lateralization indexes into the at least one machine learning model comprises:

inputting the lateralization indexes of each of the patients into the different machine learning models, and selecting one machine learning model having a highest accuracy of determining the target from the different machine learning models.

\* \* \* \* \*